(12) United States Patent
Iwata

(10) Patent No.: US 8,466,428 B2
(45) Date of Patent: Jun. 18, 2013

(54) PARTICLE BEAM IRRADIATION APPARATUS AND PARTICLE BEAM THERAPY SYSTEM

(75) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 369 days.

(21) Appl. No.: 12/875,449

(22) Filed: Sep. 3, 2010

(65) Prior Publication Data
US 2011/0101235 A1 May 5, 2011

(30) Foreign Application Priority Data

Nov. 3, 2009 (JP) .................................. 2009-252520

(51) Int. Cl.
*H01J 1/50* (2006.01)
(52) U.S. Cl.
USPC ............... 250/396 ML; 250/396 R; 250/398; 250/400; 250/492.1; 250/492.3
(58) Field of Classification Search
USPC ........... 250/396 R–398, 400, 396 ML, 492.1, 250/492.3
See application file for complete search history.

(56) References Cited

U.S. PATENT DOCUMENTS

| | | | | |
|---|---|---|---|---|
| 5,391,886 A * | 2/1995 | Yamada et al. | ........... | 250/492.22 |
| 7,122,978 B2 * | 10/2006 | Nakanishi et al. | ............ | 315/500 |
| 7,449,702 B2 * | 11/2008 | Yoshida | ..................... | 250/492.3 |
| 2003/0160189 A1 * | 8/2003 | Matsuda | .................... | 250/492.3 |
| 2006/0226372 A1 * | 10/2006 | Yanagisawa et al. | ..... | 250/396 R |
| 2009/0003524 A1 * | 1/2009 | Pu | ................................... | 378/65 |
| 2011/0105821 A1 * | 5/2011 | Dieter et al. | ..................... | 600/1 |

FOREIGN PATENT DOCUMENTS

| | | | |
|---|---|---|---|
| JP | 07148277 A | * | 6/1995 |
| JP | 2006-341010 A | | 12/2006 |
| JP | 2007-75245 A | | 3/2007 |
| WO | WO 2006/082651 A1 | | 8/2006 |

* cited by examiner

*Primary Examiner* — Michael Logie
(74) *Attorney, Agent, or Firm* — Buchanan Ingersoll & Rooney PC

(57) ABSTRACT

The objective of the present invention is to eliminate noise caused by driving a ridge filter and to achieve a uniform dose distribution without making a patient sense discomfort or anxiety. There are provided a ridge filter having a thickness distribution in which the energy that a charged particle beam loses differs depending on the position thereon through which the charged particle beam passes, a deflector that deflects the charged particle beam, and a controller that controls the deflector in such a way that the charged particle beam passes through the thickness distribution of the ridge filter.

13 Claims, 8 Drawing Sheets

PARTICLE BEAM IRRADIATION APPARATUS AND PARTICLE BEAM THERAPY SYSTEM

BACKGROUND OF THE INVENTION

1. Field of the Invention

The present invention relates to a particle beam irradiation apparatus and a particle beam therapy system for performing treatment of a cancer or the like by use of a particle beam.

2. Description of the Related Art

A particle beam therapy system is a system for performing treatment of a cancer, a tumor, and the like, by making good use of the feature, of a particle beam, that "it selectively demonstrates an effect at the deeply inner part of a body"; the contents of the technology thereof can be seen from various literatures (e.g., International Publication No. WO2006-082651/pamphlet).

The fact that "a particle beam selectively demonstrates an effect at the deeply inner part of a body" is based on the nature, of a particle beam, that it has a Bragg peak. As represented in FIG. 1 of International Publication No. WO2006-082651/pamphlet, in the case of a small-mass radiation beam such as an X-ray or a gamma ray, among various kinds of radiations, the relative dose thereof becomes maximum at a body portion near to the surface of a body and decreases as the depth from the body surface increases. In contrast, in the case of a large-mass particle beam such as a proton beam or a carbon beam, the relative dose thereof has its peak value at a position that is deep in a body and at which the beam stops, i.e., immediately before the range of the particle beam ends. The peak value is called a Bragg peak BP.

Briefly speaking, the Bragg peak suggests that "the intracorporeal place where a particle beam selectively demonstrates an effect is as narrow as a point"; however, in order to irradiate a particle beam onto an irradiation target in such a way that the dose distribution is uniform on the overall irradiation target, there is performed "enlargement of the irradiation field" of a particle beam.

The irradiation-field enlargement includes enlargement in the traveling direction (Z direction) of a particle beam and enlargement in a direction (XY-plane direction) perpendicular to the z direction. In this specification, according to International Publication No. WO2006-082651/pamphlet, the enlargement in the Z direction is referred to as "depth-direction irradiation-field enlargement", and the enlargement in the XY-plane direction is referred to as "transverse-direction irradiation-field enlargement".

Transverse-direction irradiation-field enlargement utilizing a typical passive-method is exemplified by the scatterer method. In the scatterer method, by irradiating a particle beam onto a scatterer in the particle beam irradiation unit of a particle beam irradiation apparatus, the particle beam is expanded in the transverse direction, and the middle portion, of the particle beam, in which the distribution of the dose is uniform is cut off and irradiated onto a target site. In the case where a single scatterer cannot sufficiently enlarge the uniform-dose portion, two scatterers may be utilized so that the uniform-dose portion is enlarged; this is referred to as the double scatterer method.

Transverse-direction irradiation-field enlargement utilizing a typical active-method is exemplified by the pencil beam scanning method. In the pencil beam scanning method, a particle beam is scanned in the XY plane by use of a deflection electromagnet provided at the upstream side of the particle beam irradiation unit of a particle beam irradiation apparatus and the irradiation position of the particle beam is moved as the time elapses, so that a wide irradiation field is obtained. In this method, a uniform dose distribution can be obtained by making neighboring irradiation spots of small-diameter pencil beams appropriately overlap one another. The pencil beam scanning method includes the raster method in which a particle beam is scanned in a continuous manner with respect to the time and the spot method in which a particle beam is scanned in a step manner with respect to the time. In this method, a particle beam, which is referred to as a pencil beam and, in general, has a small diameter, is directly irradiated onto a target site; however, the diameter of the pencil beam may slightly be enlarged by use of a thin scatterer.

There has been considered a method which is an intermediate between the passive method and the active method. Transverse-direction irradiation-field enlargement utilizing a typical intermediate method is exemplified by the Wobbler method. In the Wobbler method, a particle beam is scanned in the shape of a donut by use of two deflection electromagnets provided at the upstream side of the particle beam irradiation unit of a particle beam irradiation apparatus and the particle beam, which is scanned in the shape of a donut, is irradiated onto a scatterer, so that the transverse irradiation field is enlarged.

Next, irradiation-field enlargement in the depth direction will be described. As described above, the width of a Bragg peak BP in the irradiation direction of a particle beam is narrow; the irradiation-field enlargement in the depth direction denotes enlargement of the irradiation-direction width of a Bragg peak BP. The Bragg peak BP whose irradiation-direction width has been enlarged is referred to as a Spread-Out Bragg Peak SOBP.

Depth-direction irradiation-field enlargement utilizing a typical passive method is exemplified by a method utilizing ridge filter or a range modulator. In each of a ridge filter and a range modulator, the thickness of the material of an energy modulator is modulated in the irradiation direction of a particle beam. In each of a ridge filter and a range modulator, the energy of a particle beam is reduced in accordance with the modulated thickness so that the energy is changed in accordance with the modulated thickness; as a result, a particle beam, in which many kinds of intensity-changing energies are mixed, is irradiated onto an irradiation target. Because the range of a particle beam changes in accordance with the intensity of the energy, particle beams having different ranges can be irradiated onto an irradiation target. Such a passive depth-direction irradiation-field enlargement method makes it possible to obtain a Spread-Out Bragg Peak SOBP whose width is enlarged in the irradiation direction; however, the width of the Spread-Out Bragg Peak SOBP is constant and cannot be changed in the transverse directions, i.e., in the X-axis direction and the Y-axis direction that are perpendicular to the irradiation direction of a particle beam.

Accordingly, in the case where a ridge filter or a range modulator is utilized, a device named "bolus" is also utilized. As illustrated in FIG. 2 of International Publication No. WO2006-082651/pamphlet, a bolus is an energy modulator obtained by performing machining for each patient in accordance with the distal form (changing form, in the depth direction, of a site to be treated); a bolus is made of polyethylene or wax. The use of a bolus makes it possible to make the Bragg peak BP coincide with the distal form while irradiating a uniform irradiation dose over the XY plane.

In general, a ridge filter has a shape obtained by combining approximately triangular prisms, as illustrated in FIG. 2 of Japanese Patent Application Laid-Open No. 2007-75245; a ridge filter has a cross-sectional shape as illustrated in FIG. 3 of Japanese Patent Application Laid-Open No. 2007-75245; a ridge filter is integrated in an irradiation system, as illustrated in FIG. 1 of Japanese Patent Application Laid-Open No. 2007-75245.

As disclosed in Japanese Patent Application Laid-Open No. 2007-75245, there has been reported a problem that, in a particle beam therapy system utilizing a ridge filter, scattering becomes insufficient. In the case where the particle beam is a proton beam, because being relatively light, the particle beam is sufficiently scattered by air and an irradiation subject, whereby, spatially, the particle beams can sufficiently be mixed with one another in the irradiation field. However, in the case where the particle beam is a particle beam of relatively heavy particle, because scattering is not likely to occur, no uniform irradiation-dose distribution is obtained at the end of the range, and there is produced a dose valley at a position that corresponds to the ridge of a ridge filter. In other words, there has been a problem that, the dose distribution in the vicinity of the range-end position becomes a striped periodical distribution, as illustrated in FIG. 4(2) of Japanese Patent Application Laid-Open No. 2007-75245.

In order to form a uniform dose distribution at the range end of an irradiation field, Japanese Patent Application Laid-Open No. 2007-75245 discloses an apparatus in which, during irradiation of a particle beam, a ridge filter is driven in the directions that are perpendicular to the advancing direction of the particle beam so that there is solved the problem, posed when the ridge filter is utilized, that scattering becomes insufficient.

It is true that, as a prior art, there has been proposed, as disclosed in Japanese Patent Application Laid-Open No. 2007-75245, that a ridge filter is mechanically wobbled through translation or rotation so that a uniform dose distribution is effectively achieved.

However, for example, as illustrated in FIG. 1 of Japanese Patent Application Laid-Open No. 2007-75245, a ridge filter is installed in the vicinity of a patient; thus, there has been a problem that driving the ridge filter causes noise and hence the patient is made to sense discomfort or anxiety.

SUMMARY OF THE INVENTION

The objective of the present invention is to eliminate noise caused by driving a ridge filter and to achieve a uniform dose distribution that is equivalent to the dose distribution obtained by the apparatus disclosed in Japanese Patent Application Laid-Open No. 2007-75245, without making a patient sense discomfort or anxiety.

There are provided a ridge filter having a thickness distribution in which energy that a charged particle beam loses differs depending on the position thereon through which the charged particle beam passes; a deflector that deflects the charged particle beam; and a controller that controls the deflector in such a way that the charged particle beam passes through the thickness distribution of the ridge filter.

In a particle beam irradiation apparatus according to the present invention, a charged particle beam is controlled in such a way to pass through a thickness distribution, of a ridge filter, in which energy that a charged particle beam loses differs depending on the position thereon through which the charged particle beam passes; therefore, there is eliminated noise caused by driving the ridge filter, and hence a uniform dose distribution can be achieved, without making a patient sense discomfort or anxiety.

The foregoing and other object, features, aspects, and advantages of the present invention will become more apparent from the following detailed description of the present invention when taken in conjunction with the accompanying drawings.

DETAILED DESCRIPTION OF THE PREFERRED EMBODIMENTS

Embodiment 1

Figure 1:
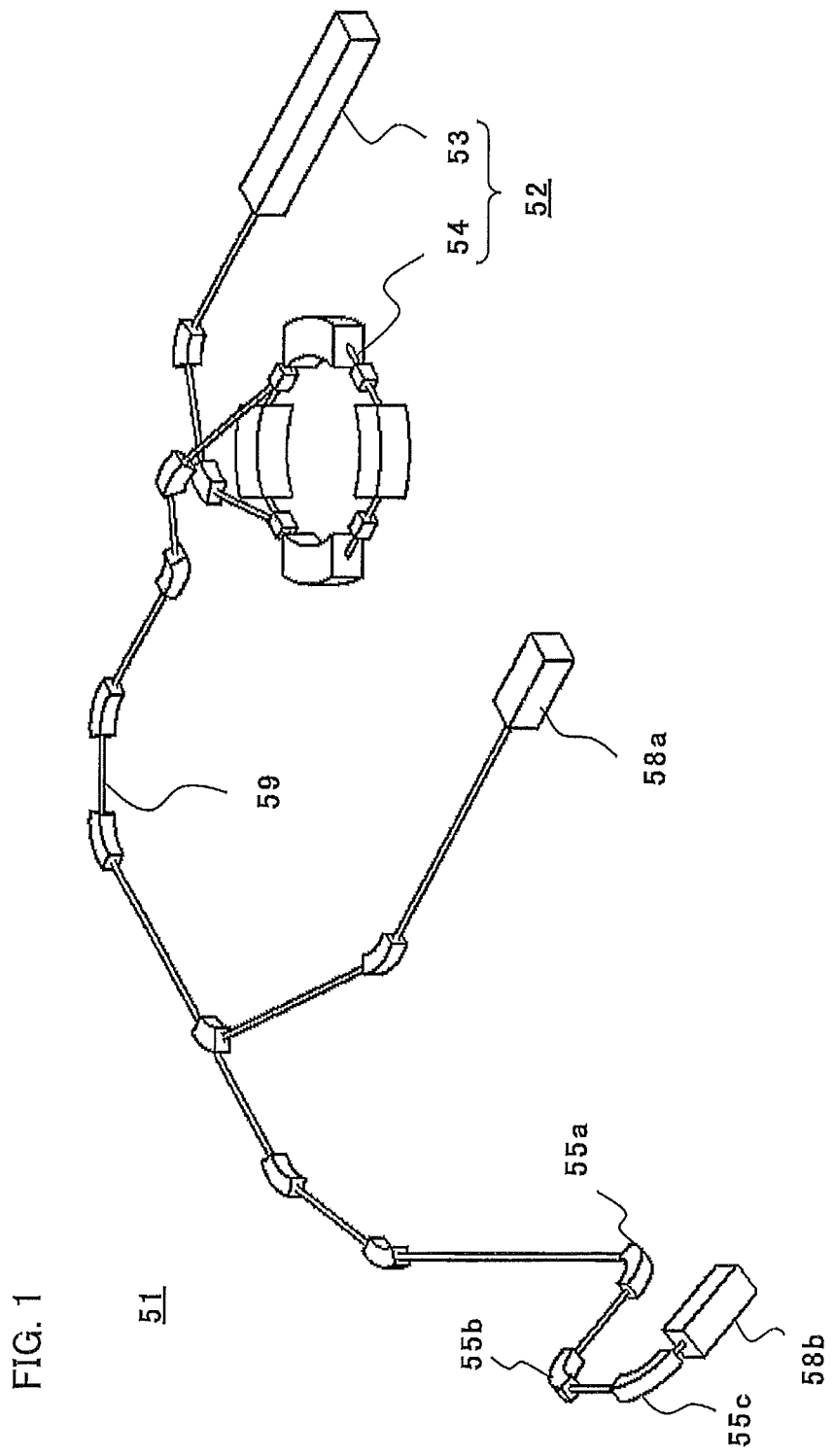
FIG. 1 is a schematic configuration diagram of a particle beam therapy system according to the present invention.
Figure 2:
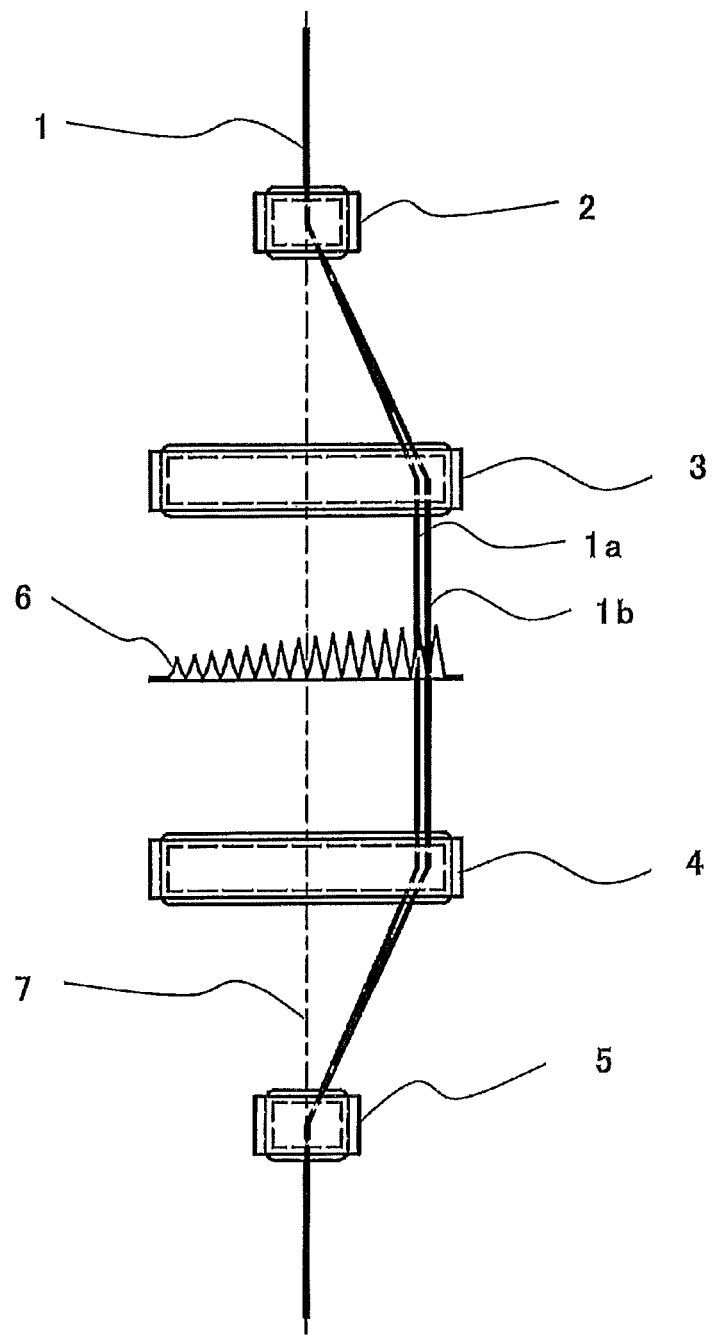
FIG. 2 is a configuration diagram illustrating the particle beam irradiation apparatus in FIG. 1.
Figure 3A:
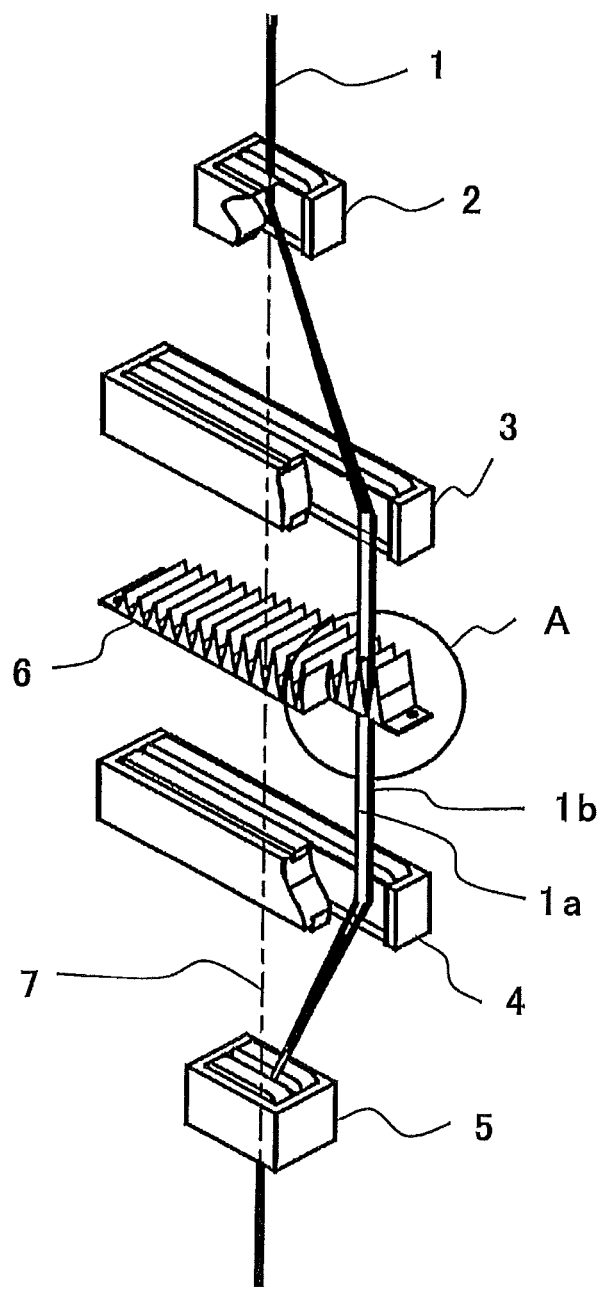
FIG. 3A is a bird's eye view illustrating the particle beam irradiation apparatus in FIG. 1.
Figure 3B:
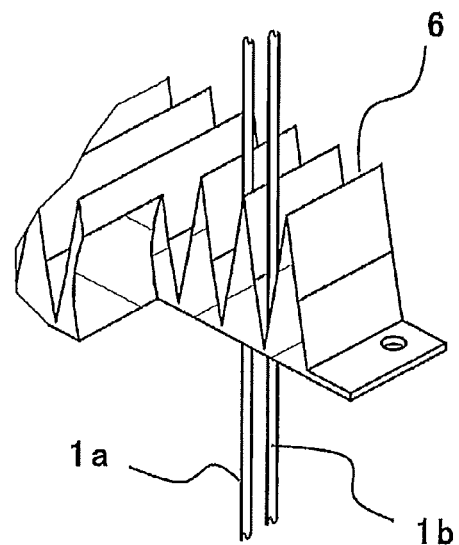
FIG. 3B is an enlarged figure of a part shown in A of FIG. 3A.

FIG. 1 is a schematic configuration diagram illustrating a particle beam therapy system according to Embodiment 1 of the present invention. FIG. 2 is a configuration diagram illustrating a particle beam irradiation apparatus; FIG. 3A is a bird's eye view of a particle beam irradiation apparatus. FIG. 3B is an enlarged figure of a part shown in A of FIG. 3A. A particle beam therapy system 51 includes an ion beam generation apparatus 52, an ion beam transport system 59, and particle beam irradiation apparatuses 58a and 58b. The ion beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the ion beam transport system 59 is to achieve transportation between the synchrotron 54 and the particle beam irradiation apparatuses 58a and 58b. A portion of the ion beam transport system 59 is provided in the rotating gantry (unillustrated), and in that portion, there are included a plurality of deflection electromagnets 55a, 55b, and 55c.

A charged particle beam 1, which is a particle beam such as a proton beam generated in ion source, is accelerated by the prestage accelerator 53 and enters the synchrotron 54. The particle beam 1 is accelerated to have predetermined energy. The charged particle beam 1 launched from the synchrotron 54 is transported to the particle beam irradiation apparatuses 58a and 58b by way of the ion beam transport system 59. The particle beam irradiation apparatuses 58a and 58b each irradiate the charged particle beam 1 onto an irradiation subject (unillustrated).

With reference to FIGS. 2 and 3, there will be explained the configuration of the particle beam irradiation apparatus in the particle beam therapy system according to Embodiment 1 of the present invention. The charged particle beam 1 generated in the ion beam generation apparatus 52 and accelerated to have predetermined energy is led to the particle beam irradiation apparatus 58 by way of the ion beam transport system 59. The particle beam irradiation apparatus 58 is configured with deflection electromagnets 2, 3, 4, and 5 that deflect the course of a beam, a ridge filter 6 that enlarges the depth-direction irradiation field, and a controller (unillustrated) that controls the deflection electromagnets 2 through 5. The deflection electromagnets 2 through 5 are deflectors; the deflection electromagnets 2 and 3 are upstream deflectors disposed at the upstream side of the ridge filter 6; the deflection electromagnets 4 and 5 are downstream deflectors disposed at the downstream side of the ridge filter 6.

In general, a ridge filter has a shape obtained by combining approximately triangular prisms, as illustrated in FIG. 2 of Japanese Patent Application Laid-Open No. 2007-75245; a ridge filter has a cross-sectional shape as illustrated in FIG. 3 of Japanese Patent Application Laid-Open No. 2007-75245. A ridge filter has a thickness distribution in which the energy that the charged particle beam 1 loses differs depending on the position through which the charged particle beam 1 passes. As illustrated in FIGS. 2 and 3, the ridge filter 6 according to Embodiment 1 of the present invention is configured with approximately triangular prisms having different heights, in order to realize various irradiation-field thicknesses in the depth direction; i.e., the ridge filter 6 is configured in such a way as to have a plurality of ridges for a different thickness distribution. As a result, by performing control as to which part of the ridge filter 6 the beam should pass through, the irradiation-field thickness in the depth direction can be changed.

The operation of the particle beam irradiation apparatus 58 will be explained. The deflection electromagnets 2, 3, 4, and 5 are utilized for realizing two functions. The first function is to deflect the charged particle beam 1 so that there is changed the passing position, on the ridge filter, of the charged particle beam 1. The second function is to wobble the charged particle beam 1 so that the dose distribution becomes uniform. In order to realize the two functions, the deflection electromagnets 2, 3, 4, and 5 are disposed in such a way as to scan the charged particle beam 1 in the same direction (in the left-and-right direction, i.e., in the X direction in FIG. 2). By combining the deflection electromagnet 2 and the deflection electromagnet 3, there can be obtained a beam whose course is parallel to the beam axis 7 of the charged particle beam 1. The respective angles at which the charged particle beam 1 is deflected by the deflection electromagnets 2 and 3 are the same but opposite to each other, and the respective angles at which the charged particle beam 1 is deflected by the deflection electromagnets 4 and 5 are the same but opposite to each other; as a result, the charged particle beam 1 can be led to an isocenter, which is an irradiation target. In FIG. 2, the direction of the beam axis 7 is the Z direction, and the direction that is perpendicular to the plane of the paper is the Y direction.

While the deflection electromagnets 2, 3, 4, and 5 are disposed in such a way as to scan the charged particle beam 1 in the same direction, the pole distance of each deflection electromagnets 2, 3, 4, and 5 can be the same, unlike the case of a wobbling electromagnet set or the scanning electromagnet set. Therefore, in spite of the electromagnet located downstream of other electromagnet, the pole distance can be kept narrow, meaning that the power source for driving the electromagnet can also be kept small.

The controller (unillustrated) controls the deflection electromagnets 2 through 5 in such a way that the respective angles at which the charged particle beam 1 is deflected by the deflection electromagnets 2 and 3 are the same but opposite to each other, and the respective angles at which the charged particle beam 1 is deflected by the deflection electromagnets 4 and 5 are the same but opposite to each other. As a result, the first function is realized. In addition, the controller controls the deflection electromagnets 2 through 5 in such a way as to wobble the charged particle beam 1, i.e., specifically, in such a way that, in FIG. 2, the charged particle beam 1 repeats the state a and the state b that are in the relationship where the respective corresponding positions of the charged particle beam 1 are spaced apart from each other by at least a pitch of ridges of the ridge filter 6; that is to say, the deflection electromagnets 2 through 5 are controlled in such a way that a charged particle beam 1a and a charged particle beam 1b are repeated. As a result, the second function is realized. It is only necessary that the charged particle beam 1 is wobbled between the state of the charged particle beam 1a and the state of the charged particle beam 1b at least once within a time in which the charged particle beam 1 is irradiated over a single spot.

Because, in the particle beam irradiation apparatus 58 according to Embodiment 1, the charged particle beam 1 is wobbled in such a way as to pass through different positions on the ridge filter 6, it is not required to drive the ridge filter 6. Thus, there is eliminated noise caused by driving the ridge filter 6, and hence a uniform dose distribution, which is equivalent to the dose distribution obtained by the apparatus disclosed in Japanese Patent Application Laid-Open No. 2007-75245, can be achieved, without making a patient sense discomfort or anxiety.

Because, in the particle beam irradiation apparatus 58 according to Embodiment 1, the deflection electromagnet at the upstream side of the ridge filter 6 is configured with a pair of deflection electromagnets 2 and 3, there is obtained a parallel beam that is parallel to the beam axis 7 of the charged particle beam 1. The charged particle beam 1 that passes through the ridge filter 6 is a parallel beam that is parallel to the beam axis 7, so that the beam diameter can be made smaller than that in the case where the charged particle beam 1 passes through the ridge filter 6 at an angle. The foregoing configuration is effective in the case where there is obtained a dose distribution that is uniform in the depth direction and in which the beam diameter is small.

In the particle beam irradiation apparatus 58 according to Embodiment 1, there is provided the ridge filter 6 having a plurality of ridges for a different thickness distribution, i.e., many kinds of ridges, and the upstream deflection electromagnets 2 and 3 are controlled in such a way that the charged particle beam 1 changes its passing positions on the ridge filter 6; therefore, it is not required to change ridge filters for each patient, whereby the time for changing ridge filters is saved. Even in the case of a diseased site having different thicknesses, the time for changing ridge filters can be saved by changing the passing positions on the ridge filter 6; thus, irradiation can be performed in a short time.

In the particle beam irradiation apparatus 58 according to Embodiment 1, a pair of deflection electromagnets 2 and 3, which are disposed at the upstream side of the ridge filter 6, and a pair of deflection electromagnets 4 and 5, which are disposed at the downstream side of the ridge filter 6, i.e., two pairs of (upstream and downstream) deflection electromagnets are utilized in such a way that the respective angles of the charged particle beam 1 that is deflected by the upstream deflection electromagnets are the same but opposite to each other and the respective angles of the charged particle beam 1 that is deflected by the downstream deflection electromagnets are the same but opposite to each other, so that the isocenter of the particle beam irradiation apparatus 58 can be prevented from fluctuating. Because the isocenter does not fluctuate, it is not required to move a patient as the isocenter shifts; thus, the time for irradiation positioning can be shortened.

Figure 4:
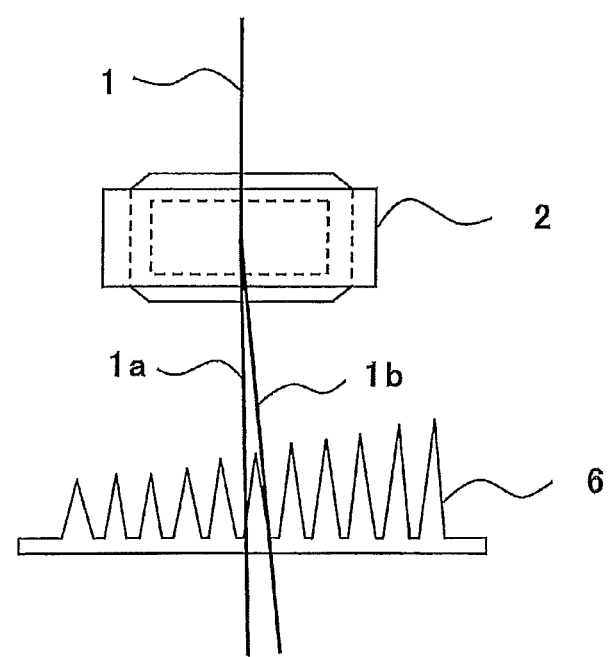
FIG. 4 is a configuration diagram illustrating other particle beam irradiation apparatus than the particle beam irradiation apparatus in FIG. 1.

Even when the charged particle beam 1 is wobbled by only the deflection electromagnet 2, which deflects the charged particle beam 1, in such a way that the charged particle beam 1 passes through different positions on the ridge filter 6, it is not required to drive the ridge filter 6. FIG. 4 is a configuration diagram illustrating another particle beam irradiation apparatus. The charged particle beam 1 is deflected and its passing positions on the ridge filter are changed so that the charged particle beam 1 is wobbled in such a way that the charged particle beam 1a and the charged particle beam 1b are repeated; thus, the dose distribution can be made uniform in the depth direction. Compared with the particle beam irradiation apparatus in FIG. 2, the diameter of the charged particle beam 1 that passes through the ridge filter 6 becomes large; however, the particle beam irradiation apparatus in FIG. 4 has an advantage of reducing the number of deflection electromagnets. Thus, the particle beam irradiation apparatus illustrated in FIG. 4 can eliminate noise caused by driving the ridge filter 6 and hence can achieve a uniform dose distribution, which is equivalent to the dose distribution obtained by the apparatus disclosed in Japanese Patent Application Laid-Open No. 2007-75245, without making a patient sense discomfort or anxiety.

As described above, in the particle beam irradiation apparatus 58 according to Embodiment 1, there are provided the ridge filter 6 having a thickness distribution where the energy that the charged particle beam 1 loses differs depending on the position through which the charged particle beam 1 passes, the deflector 2 that deflects the charged particle beam 1, and the controller that controls the deflector 2 in such a way that the charged particle beam 1 passes through the thickness distribution of the ridge filter 6; therefore, there is eliminated noise caused by driving the ridge filter 6, and hence a uniform dose distribution can be achieved, without making a patient sense discomfort or anxiety.

In the particle beam therapy system 51 according to Embodiment 1, there are provided the ion beam generation apparatus 52 that generates the charged particle beam 1 and accelerates it by means of the accelerator 54 until it acquires predetermined energy, the ion beam transport system 59 that transports the charged particle beam 1 accelerated by the ion beam generation apparatus 52, and the particle beam irradiation apparatus 58 that irradiates the charged particle beam 1 transported by the ion beam transport system 59 onto an irradiation subject; and the particle beam irradiation apparatus is provided with the ridge filter 6 having a thickness distribution in which the energy that the charged particle beam loses differs depending on the position through which the charged particle beam 1 passes, the deflector 2 that deflects the charged particle beam 1, and the controller that controls the deflector 2 in such a way that the charged particle beam 1 passes through the thickness distribution of the ridge filter 6. As a result, there is eliminated noise caused by driving the ridge filter, and hence a particle beam therapy utilizing a charged particle beam in a uniform dose distribution can be realized without making a patient sense discomfort or anxiety.

Additionally, the above explanation has been implemented assuming that the charged particle beam 1a and the charged particle beam 1b are spaced apart from each other by a pitch of ridges of the ridge filter 6; in the case where there exists a plurality of continuous ridges having the same heights, a uniform dose distribution can be obtained when the controller performs control in such a way that the charged particle beam 1a and the charged particle beam 1b are spaced apart from each other by more than a pitch of ridges.

The angle of the charged particle beam 1 deflected by the downstream deflection electromagnet may be different from the angle of the charged particle beam 1 deflected by the upstream deflection electromagnet. The beam diameter of the charged particle beam 1 is narrowed by the downstream deflection electromagnet, so that there can be obtained a dose distribution that is uniform in the depth direction and in which there are included small-diameter beams that are parallel to one another.

Embodiment 2

Figure 5:
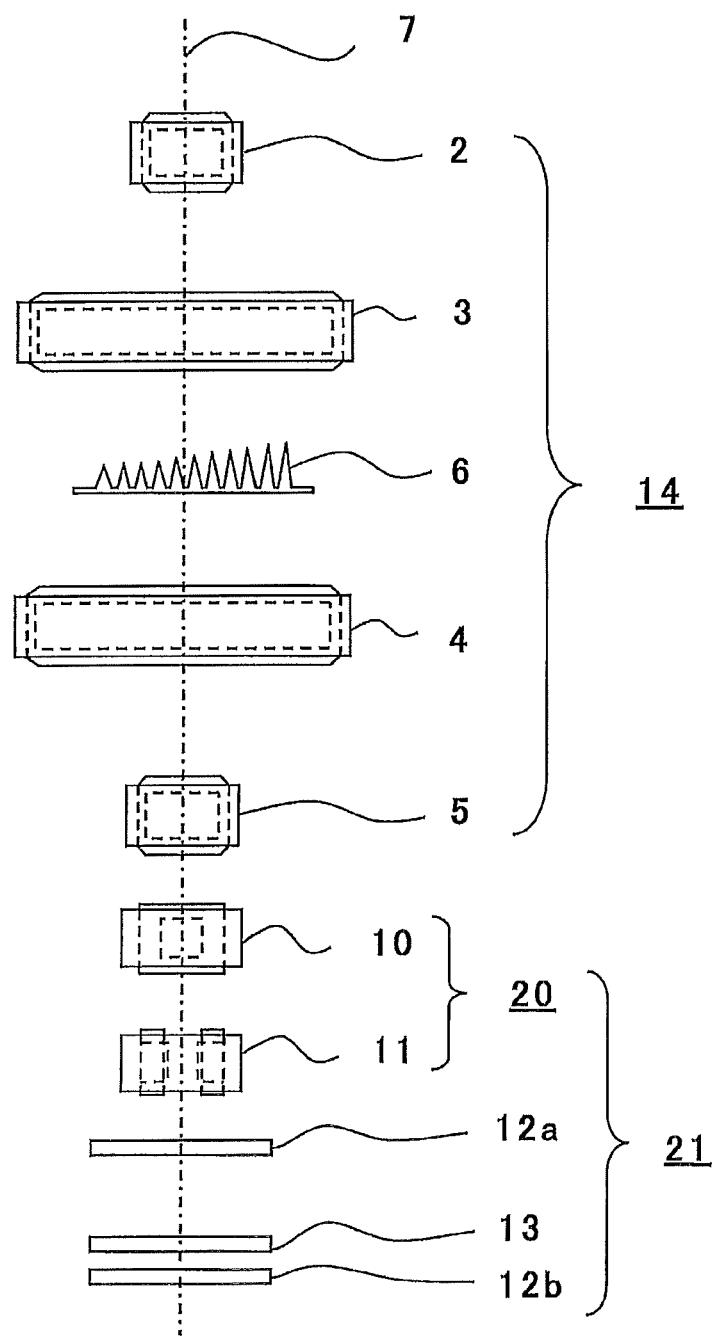
FIG. 5 is a configuration diagram illustrating a particle beam irradiation apparatus according to Embodiment 2 of the present invention.

FIG. 5 is a configuration diagram illustrating a particle beam irradiation apparatus according to Embodiment 2 of the present invention. The particle beam irradiation apparatus according to Embodiment 2 is different from the particle beam irradiation apparatus according to Embodiment 1 in that it has an irradiation system 21 utilized in the pencil beam scanning method. The irradiation system 21 utilized in the pencil beam scanning method includes a transverse-direction irradiation field enlargement unit 20, position monitors 12a and 12b that detect the passing position of the charged particle beam 1, and a dose monitor 13 that detects the dose of the charged particle beam 1. The transverse-direction irradiation field enlargement unit 20 includes an X-direction scanning electromagnet 10, a Y-direction scanning electromagnet 11, and a scanning power source (unillustrated) that outputs the control inputs of the X-direction scanning electromagnet 10 and the Y-direction scanning electromagnet 11. The X-direction scanning electromagnet 10 and the Y-direction scanning electromagnet 11 each serve as a beam scanning unit. A depth-direction irradiation field enlargement unit 14 includes the deflection electromagnets 2 through 4, the ridge filter 6, and the unillustrated controller. The depth-direction irradiation field enlargement unit 14 is configured in the same manner as the particle beam irradiation apparatus explained in Embodiment 1.

In the transverse-direction irradiation field enlargement unit 20, a particle beam is scanned in the XY plane by use of the X-direction scanning electromagnet 10 and the Y-direction scanning electromagnet 11 and the irradiation position of the particle beam is moved as the time elapses, so that a wide irradiation field is obtained in the transverse direction.

The particle beam irradiation apparatus 58 according to Embodiment 2 includes the depth-direction irradiation field enlargement unit 14 and the irradiation system 21 utilized in the pencil beam scanning method; therefore, there is eliminated noise caused by driving the ridge filter, and hence irradiation-field enlargement in the depth direction and the transverse direction can be achieved while ensuring a uniform dose distribution, without making a patient sense discomfort or anxiety.

Embodiment 3

Figure 6:
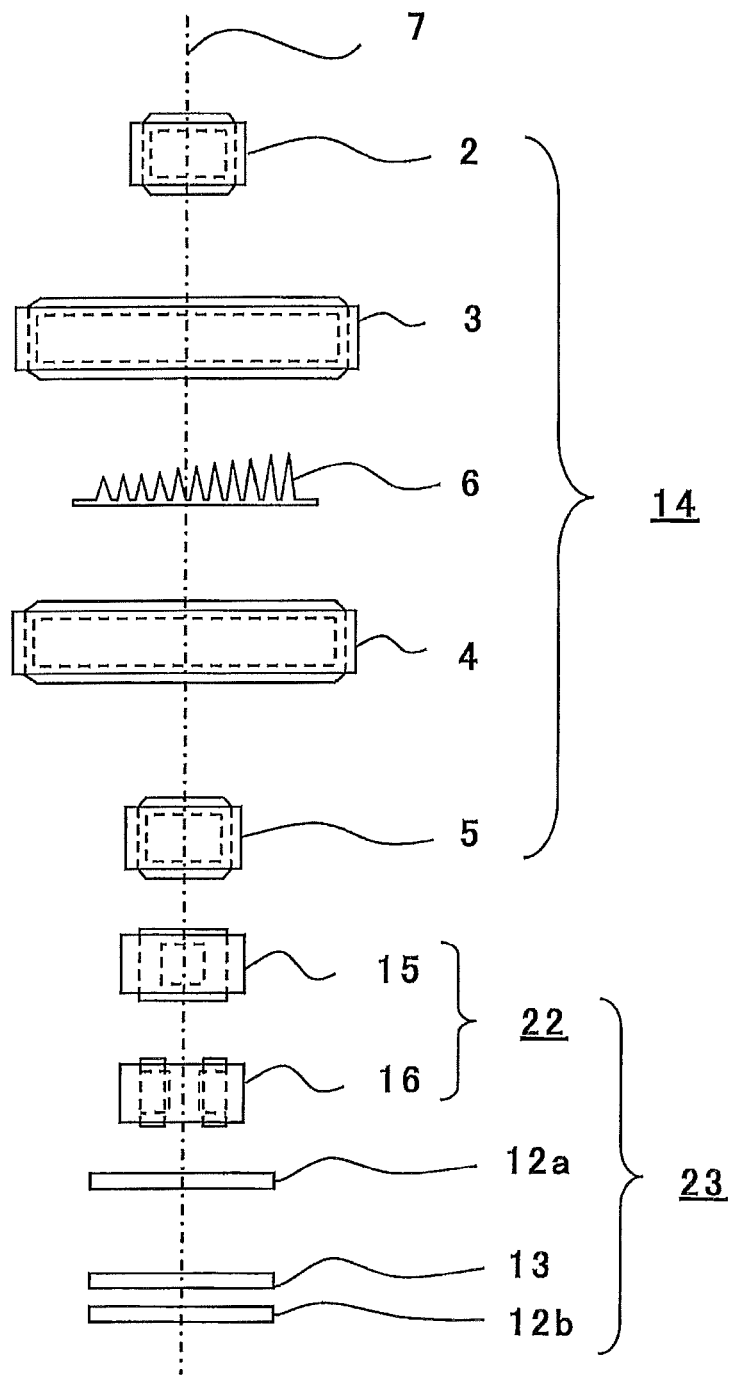
FIG. 6 is a configuration diagram illustrating a particle beam irradiation apparatus according to Embodiment 3 of the present invention.

FIG. 6 is a configuration diagram illustrating a particle beam irradiation apparatus according to Embodiment 3 of the present invention. The particle beam irradiation apparatus according to Embodiment 3 is different from the particle beam irradiation apparatus according to Embodiment 2 in that it has an irradiation system 23 utilized in the Wobbler method. The irradiation system 23 utilized in the Wobbler method includes a transverse-direction irradiation field enlargement unit 22, the position monitors 12a and 12b that detect the passing position of the charged particle beam 1, and the dose monitor 13 that detects the dose of the charged particle beam 1. The transverse-direction irradiation field enlargement unit 22 includes an X-direction wobbler electromagnet 15, a Y-direction wobbler electromagnet 16, and a scanning power source (unillustrated) that outputs the control inputs of the X-direction wobbler electromagnet 15 and the Y-direction wobbler electromagnet 16. The X-direction wobbler electromagnet 15 and the Y-direction wobbler electromagnet 16 each serve as a beam scanning unit. Although unillustrated, a scatterer, a collimator, a range shifter, a bolus, and the like are arranged.

In the transverse-direction irradiation field enlargement unit 22, a particle beam is scanned in the XY plane in the shape of a donut by use of the X-direction wobbler electromagnet 15 and the Y-direction wobbler electromagnet 16 and the particle beam 1 that is scanned in the shape of a donut is irradiated onto a scatterer, so that a wide irradiation field is obtained in the transverse direction.

The particle beam irradiation apparatus 58 according to Embodiment 3 includes the depth-direction irradiation field enlargement unit 14 and the irradiation system 23 utilized in the Wobbler method; therefore, there is eliminated noise caused by driving the ridge filter, and hence irradiation-field enlargement in the depth direction and the transverse direction can be achieved while ensuring a uniform dose distribution, without making a patient sense discomfort or anxiety.

Embodiment 4

Figure 7:
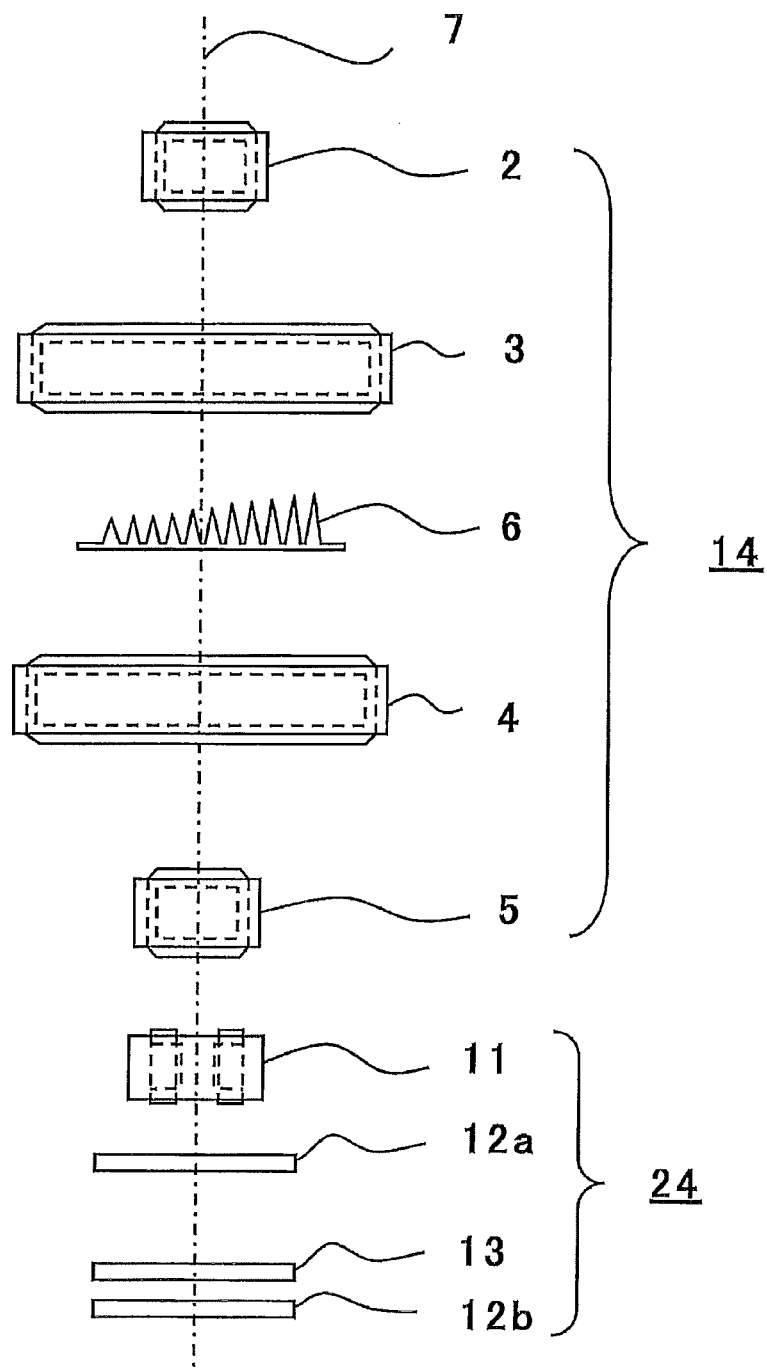
FIG. 7 is a configuration diagram illustrating a particle beam irradiation apparatus according to Embodiment 4 of the present invention.

FIG. 7 is a configuration diagram illustrating a particle beam irradiation apparatus according to Embodiment 4 of the present invention. The particle beam irradiation apparatus according to Embodiment 4 is different from the particle beam irradiation apparatus according to Embodiment 2 in that an irradiation system 24 utilized in the pencil beam scanning method does not have the X-direction scanning electromagnet 10. The downstream deflection electromagnets 4 and 5 in the depth-direction irradiation field enlargement unit 14 are each utilized also as an X-direction scanning electromagnet utilized in the pencil beam scanning method. In this case, the deflection electromagnet 5 corresponds to the X-direction scanning electromagnet, and the deflection electromagnet 4 corresponds to the X-direction downstream deflector that deflects a particle beam in such a way as to lead it to the X-direction scanning electromagnet.

The downstream deflection electromagnets 4 and 5 in the depth-direction irradiation field enlargement unit 14 are each utilized also as an X-direction scanning electromagnet utilized in the pencil beam scanning method; therefore, the pencil beam scanning method can be realized in the particle beam irradiation apparatus according to Embodiment 4, even by utilizing only the Y-direction scanning electromagnet 11 as the scanning electromagnet in the irradiation system 24 utilized in the pencil beam scanning method.

The particle beam irradiation apparatus 58 according to Embodiment 4 can be downsized compared with the particle beam irradiation apparatus according to Embodiment 2. Accordingly, with a particle beam irradiation apparatus smaller than the particle beam irradiation apparatus according to Embodiment 2, there is eliminated noise caused by driving the ridge filter, and hence irradiation-field enlargement in the depth direction and the transverse direction can be achieved while ensuring a uniform dose distribution, without making a patient sense discomfort or anxiety.

Embodiment 5

Figure 8:
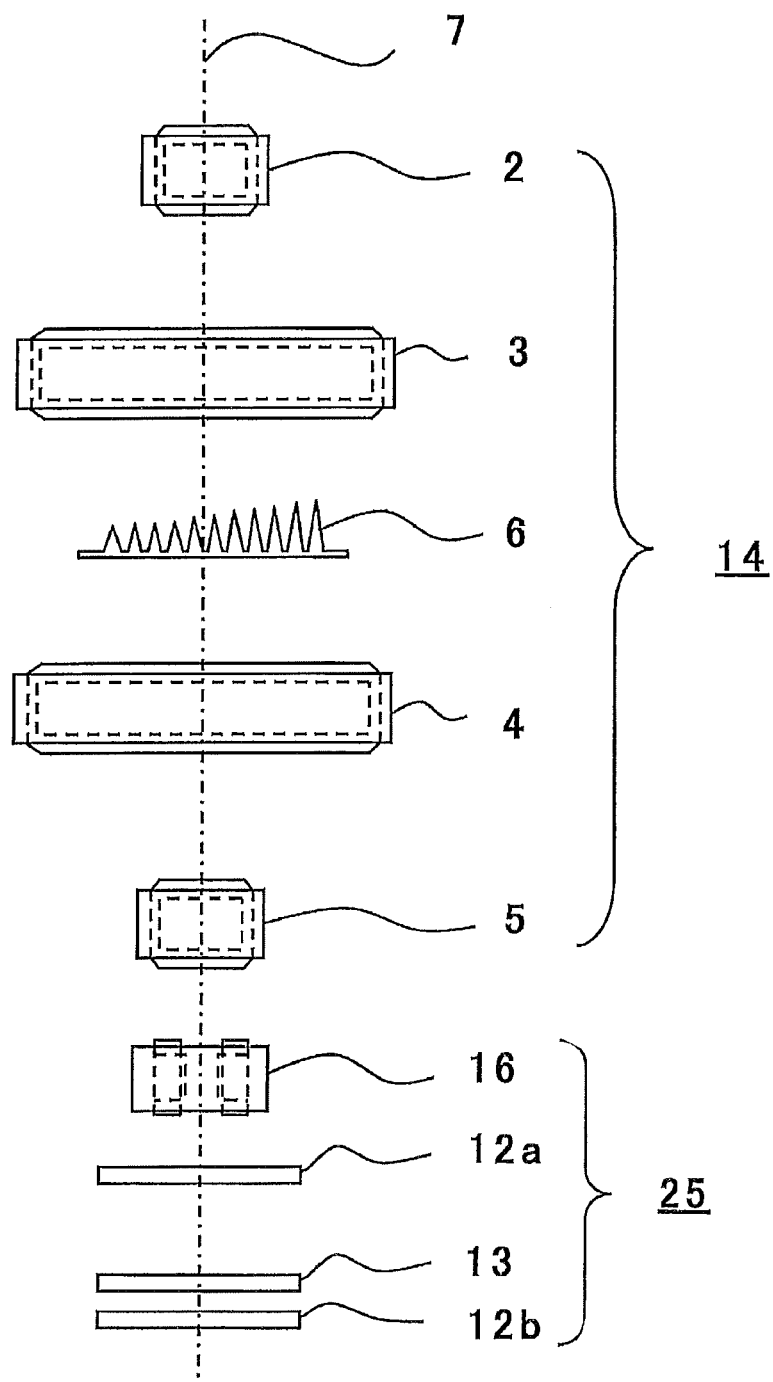
FIG. 8 is a configuration diagram illustrating a particle beam irradiation apparatus according to Embodiment 5 of the present invention.

FIG. 8 is a configuration diagram illustrating a particle beam irradiation apparatus according to Embodiment 5 of the present invention. The particle beam irradiation apparatus according to Embodiment 5 is different from the particle beam irradiation apparatus according to Embodiment 3 in that an irradiation system 25 utilized in the Wobbler method does not have the X-direction wobbler electromagnet 15. The downstream deflection electromagnets 4 and 5 in the depth-direction irradiation field enlargement unit 14 are each utilized also as an X-direction wobbler electromagnet utilized in the Wobbler method. In this case, the deflection electromagnet 5 corresponds to the X-direction wobbler electromagnet, and the deflection electromagnet 4 corresponds to the X-direction downstream deflector that deflects a particle beam in such a way as to lead it to the X-direction wobbler electromagnet.

The downstream deflection electromagnets 4 and 5 in the depth-direction irradiation field enlargement unit 14 are each utilized also as an X-direction wobbler electromagnet utilized in the Wobbler method; therefore, the Wobbler method can be realized in the particle beam irradiation apparatus according to Embodiment 5, even by utilizing only the Y-direction wobbler electromagnet 16 as the wobbler electromagnet in the irradiation system 25 utilized in the Wobbler method.

The particle beam irradiation apparatus 58 according to Embodiment 5 can be downsized compared with the particle beam irradiation apparatus according to Embodiment 3. Accordingly, with a particle beam irradiation apparatus smaller than the particle beam irradiation apparatus according to Embodiment 3, there is eliminated noise caused by driving the ridge filter, and hence irradiation-field enlargement in the depth direction and the transverse direction can be achieved while ensuring a uniform dose distribution, without making a patient sense discomfort or anxiety.

Various modifications and alterations of this invention will be apparent to those skilled in the art without departing from the scope and spirit of this invention, and it should be understood that this is not limited to the illustrative embodiments set forth herein.

What is claimed is:

1. A particle beam irradiation apparatus that irradiates a charged particle beam accelerated by an accelerator onto an irradiation subject, the particle beam irradiation apparatus comprising:
 a ridge filter having a thickness distribution in which energy that the charged particle beam loses differs depending on the position thereon through which the charged particle beam passes;
 an upstream deflector that is disposed at an upstream side of the ridge filter and includes a first upstream deflector that deflects the charged particle beam in a direction that departs from a beam axis along which the charged particle beam enters and a second upstream deflector that is disposed at a downstream side of the first upstream deflector and deflects the charged particle beam in a direction parallel to the beam axis;
 a downstream deflector that is disposed at a downstream side of the ridge filter and includes a first downstream deflector that deflects the charged particle beam toward the beam axis along which the charged particle beam enters and a second downstream deflector that is disposed at a downstream side of the first downstream deflector and deflects the charged particle beam in a direction parallel to the beam axis; and a controller that controls the upstream and downstream deflectors in such a way that the charged particle beam, with a wobbling motion, passes through the thickness distribution of the ridge filter, wherein the first and second downstream deflectors deflect the charged particle beam in a same plane in which the first and second upstream deflectors deflect the charged particle beam.

2. The particle beam irradiation apparatus according to claim 1, wherein the downstream deflector makes the course of the charged particle beam coincide with the beam axis along which the charged particle beam enters.

3. The particle beam irradiation apparatus according to claim 2, further including a beam scanning unit, disposed at the downstream side of the downstream deflector, that scans the charged particle beam in the XY plane that intersects the beam axis along which the charged particle beam enters.

4. The particle beam irradiation apparatus according to claim 1, further including a beam scanning unit, disposed at the downstream side of the ridge filter, that scans the charged particle beam in the XY plane that intersects the beam axis along which the charged particle beam enters.

5. The particle beam irradiation apparatus according to claim 4, wherein the beam scanning unit includes an X-direction scanning electromagnet that scans the charged particle beam in the X direction and a Y-direction scanning electromagnet that scans the charged particle beam in the Y direction.

6. The particle beam irradiation apparatus according to claim 4, wherein the beam scanning unit includes an X-direction wobbler electromagnet and a Y-direction wobbler electromagnet that make the charged particle beam rotate around the beam axis.

7. The particle beam irradiation apparatus according to claim 1, further including a beam scanning unit, disposed at the downstream side of the downstream deflector, that scans the charged particle beam in the XY plane that intersects the beam axis along which the charged particle beam enters.

8. The particle beam irradiation apparatus according to claim 7, wherein the beam scanning unit includes an X-direction scanning electromagnet that scans the charged particle beam in the X direction and a Y-direction scanning electromagnet that scans the charged particle beam in the Y direction.

9. The particle beam irradiation apparatus according to claim 1, further including a beam scanning unit, disposed at the downstream side of the ridge filter, that scans the charged particle beam in the XY plane that intersects the beam axis along which the charged particle beam enters, wherein the beam scanning unit includes (i) an X-direction beam scanning unit that is disposed in the vicinity of the ridge filter and scans the charged particle beam in the X direction and (ii) a Y-direction scanning electromagnet that scans the charged particle beam in the Y direction, and the X-direction beam scanning unit includes (i) an X-direction scanning electromagnet that scans the charged particle beam in the X direction and (ii) an X-direction downstream deflector that is disposed at the upstream side of the X-direction scanning electromagnet and deflects the charged particle beam in such a way as to lead the charged particle beam that has passed through the ridge filter to the X-direction scanning electromagnet.

10. The particle beam irradiation apparatus according to claim 1, further including a beam scanning unit, disposed at the downstream side of the ridge filter, that scans the charged particle beam in the XY plane that intersects the beam axis along which the charged particle beam enters, wherein the beam scanning unit includes an X-direction wobbler electromagnet and a Y-direction wobbler electromagnet that make the charged particle beam rotate around the beam axis, the X-direction wobbler electromagnet is disposed in the vicinity of the ridge filter, and the beam scanning unit has an X-direction downstream deflector that is disposed at the upstream side of the X-direction wobbler electromagnet and deflects the charged particle beam in such a way as to lead the charged particle beam that has passed through the ridge filter to the X-direction wobbler electromagnet.

11. The particle beam irradiation apparatus according to claim 1, wherein the ridge filter has a plurality of ridges in the thickness distribution.

12. A particle beam therapy system comprising:

an ion beam generation apparatus that generates a charged particle beam and accelerates the charged particle beam by means of an accelerator until the charged particle beam acquires predetermined energy;

an ion beam transport system that transports the charged particle beam accelerated by the ion beam generation apparatus; and a particle beam irradiation apparatus that irradiates the charged particle beam transported by the ion beam transport system onto an irradiation subject, wherein the particle beam irradiation apparatus is a particle beam irradiation apparatus according to claim 1.

13. The particle beam irradiation apparatus according to claim 1, wherein the first and second upstream deflectors and the first and second downstream deflectors deflect the charged particle beam to pass through the ridge filter while the charged particle beam is irradiated over the same spot.

* * * * *